(12) United States Patent
Love

(10) Patent No.: US 8,038,721 B2
(45) Date of Patent: Oct. 18, 2011

(54) SOFT TISSUE FILLER

(76) Inventor: Anna Love, La Mesa, CA (US)

( * ) Notice: Subject to any disclaimer, the term of this patent is extended or adjusted under 35 U.S.C. 154(b) by 179 days.

(21) Appl. No.: 12/337,143

(22) Filed: Dec. 17, 2008

(65) Prior Publication Data
US 2009/0156709 A1 Jun. 18, 2009

Related U.S. Application Data

(60) Provisional application No. 61/014,282, filed on Dec. 17, 2007.

(51) Int. Cl.
A61F 2/02 (2006.01)
(52) U.S. Cl. .................................... 623/23.72
(58) Field of Classification Search .................. 424/489; 514/789; 623/23, 73, 23.72
See application file for complete search history.

(56) References Cited

U.S. PATENT DOCUMENTS

| 3,882,198 | A | * | 5/1975 | Miller | 525/227 |
|---|---|---|---|---|---|
| 4,080,344 | A | * | 3/1978 | Ikeda et al. | 521/60 |
| 4,433,073 | A | * | 2/1984 | Sano et al. | 523/201 |
| 4,500,658 | A | * | 2/1985 | Fox | 523/117 |
| 4,654,039 | A | | 3/1987 | Brandt et al. | |
| 5,278,233 | A | * | 1/1994 | Abe et al. | 525/74 |
| 5,328,962 | A | * | 7/1994 | Shen | 525/228 |
| 5,344,452 | A | * | 9/1994 | Lemperle | 623/23.73 |
| 5,451,406 | A | * | 9/1995 | Lawin et al. | 424/423 |
| 5,540,912 | A | * | 7/1996 | Roorda et al. | 424/422 |
| 5,633,001 | A | * | 5/1997 | Ågerup | 424/423 |
| 5,635,215 | A | * | 6/1997 | Boschetti et al. | 424/501 |
| 5,648,100 | A | * | 7/1997 | Boschetti et al. | 424/501 |
| 5,792,478 | A | * | 8/1998 | Lawin et al. | 424/502 |
| 5,798,113 | A | * | 8/1998 | Dionne et al. | 424/422 |
| 5,919,234 | A | * | 7/1999 | Lemperle et al. | 623/23.72 |
| 5,922,025 | A | * | 7/1999 | Hubbard | 424/423 |
| 5,922,507 | A | * | 7/1999 | Van Damme et al. | 430/273.1 |
| 5,976,500 | A | * | 11/1999 | Unger | 424/9.32 |
| 6,280,473 | B1 | * | 8/2001 | Lemperle et al. | 623/16.11 |
| 6,391,059 | B1 | * | 5/2002 | Lemperle et al. | 623/23.5 |
| 6,432,437 | B1 | * | 8/2002 | Hubbard | 424/424 |
| 6,436,424 | B1 | * | 8/2002 | Vogel et al. | 424/422 |
| 6,558,612 | B1 | * | 5/2003 | Hubbard | 264/654 |
| 6,660,301 | B1 | * | 12/2003 | Vogel et al. | 424/489 |
| 6,685,963 | B1 | * | 2/2004 | Taupin et al. | 424/486 |
| 6,712,851 | B1 | * | 3/2004 | Lemperle et al. | 623/16.11 |
| 6,759,449 | B2 | * | 7/2004 | Kimura et al. | 523/118 |
| 6,759,463 | B2 | * | 7/2004 | Lorah et al. | 524/445 |
| 6,790,456 | B2 | * | 9/2004 | Vogel et al. | 424/423 |

(Continued)

FOREIGN PATENT DOCUMENTS

EP 0826381 3/1998

(Continued)

Primary Examiner — James J Seidleck
Assistant Examiner — Peter A Salamon
(74) Attorney, Agent, or Firm — Gottlieb, Rackman & Reisman, P.C.

(57) ABSTRACT

An improved non-toxic soft tissue filler is provided. The soft non-toxic tissue filler consists of spherically shaped solid particles having a textured surface of a size range of between about 32 and 90 microns (depending on the concentration that is desired). The particles are suspended evenly in a gel as a carrier. The solid particles are preferably a non-ceramic cured polymer such as polymethylmethacrylate (PMMA). The gel is a combination of a cellulose polysaccharide such as carboxymethylcellulose (CMC) and an alcohol such as polyvinyl alcohol (PVA) dissolved in water or some other solvent. The filler is used by injection in order to augment a patient's soft tissue as well as to correct soft tissue defects.

23 Claims, 3 Drawing Sheets

U.S. PATENT DOCUMENTS

| | | | |
|---|---|---|---|
| 6,838,507 B2* | 1/2005 | Chou et al. | 524/445 |
| 6,869,599 B2* | 3/2005 | Tournilhac et al. | 424/64 |
| 6,914,095 B2* | 7/2005 | Lorah et al. | 524/445 |
| 6,998,107 B2* | 2/2006 | Unger | 424/9.4 |
| 7,014,971 B2* | 3/2006 | Skorokhod et al. | 430/111.32 |
| 7,060,287 B1* | 6/2006 | Hubbard et al. | 424/423 |
| 7,109,254 B2* | 9/2006 | Muller et al. | 523/105 |
| 7,131,997 B2* | 11/2006 | Bourne et al. | 623/23.72 |
| 7,183,334 B2* | 2/2007 | Guzauskas | 522/31 |
| 7,192,984 B2* | 3/2007 | Berg et al. | 514/781 |
| 7,199,171 B2* | 4/2007 | Sakamoto | 524/394 |
| 7,211,613 B2* | 5/2007 | Lorah et al. | 524/445 |
| 7,259,203 B2* | 8/2007 | Chou et al. | 524/445 |
| 7,291,665 B2* | 11/2007 | Lorah et al. | 524/445 |
| 7,314,636 B2 | 1/2008 | Caseres et al. | |
| 2002/0004548 A1* | 1/2002 | Smith et al. | 524/493 |
| 2002/0016637 A1* | 2/2002 | Anton | 623/23.73 |
| 2002/0055581 A1* | 5/2002 | Lorah et al. | 524/445 |
| 2002/0058739 A1* | 5/2002 | Lorah et al. | 524/445 |
| 2002/0058740 A1* | 5/2002 | Lorah et al. | 524/445 |
| 2002/0086908 A1* | 7/2002 | Chou et al. | 516/98 |
| 2002/0120348 A1* | 8/2002 | Melican et al. | 623/23.72 |
| 2002/0150550 A1* | 10/2002 | Petersen | 424/78.31 |
| 2003/0044440 A1* | 3/2003 | Toumi | 424/401 |
| 2003/0050359 A1* | 3/2003 | Kimura et al. | 522/182 |
| 2003/0050366 A1* | 3/2003 | Giberti et al. | 523/223 |
| 2003/0147935 A1* | 8/2003 | Binette et al. | 424/423 |
| 2003/0220413 A1* | 11/2003 | Petereit et al. | 523/105 |
| 2004/0047892 A1* | 3/2004 | Desrosiers et al. | 424/423 |
| 2004/0063616 A1* | 4/2004 | Patt | 514/6 |
| 2004/0138759 A1* | 7/2004 | Muller et al. | 623/23.62 |
| 2004/0180281 A1* | 9/2004 | Skorokhod et al. | 430/111.1 |
| 2004/0191323 A1* | 9/2004 | Asius et al. | 424/489 |
| 2004/0220317 A1* | 11/2004 | Lorah et al. | 524/445 |
| 2005/0026063 A1* | 2/2005 | Komoto et al. | 430/109.1 |
| 2005/0059769 A1* | 3/2005 | Chou et al. | 524/445 |
| 2005/0148716 A1* | 7/2005 | Sakamoto | 524/394 |
| 2005/0175704 A1* | 8/2005 | Petersen | 424/486 |
| 2005/0186240 A1* | 8/2005 | Ringeisen et al. | 424/423 |
| 2005/0226030 A1* | 10/2005 | Kato et al. | 365/154 |
| 2005/0226936 A1 | 10/2005 | Agerup | |
| 2005/0281883 A1* | 12/2005 | Daniloff et al. | 424/489 |
| 2005/0287180 A1* | 12/2005 | Chen | 424/400 |
| 2006/0093644 A1* | 5/2006 | Quelle et al. | 424/423 |
| 2006/0222677 A1* | 10/2006 | Baroli et al. | 424/422 |
| 2006/0247610 A1* | 11/2006 | Lanphere et al. | 606/21 |
| 2006/0280769 A1* | 12/2006 | Chu et al. | 424/423 |
| 2007/0026030 A1 | 2/2007 | Gill et al. | |
| 2007/0071789 A1* | 3/2007 | Pantelidis et al. | 424/423 |
| 2007/0077544 A1* | 4/2007 | Lemperle et al. | 434/262 |
| 2007/0184087 A1* | 8/2007 | Voigts et al. | 424/423 |
| 2007/0196421 A1* | 8/2007 | Hunter et al. | 424/423 |
| 2007/0287095 A1* | 12/2007 | Endo | 430/270.1 |
| 2007/0292470 A1* | 12/2007 | Thornton | 424/423 |

FOREIGN PATENT DOCUMENTS

| | | |
|---|---|---|
| WO | WO90/06093 | 6/1990 |
| WO | WO/9633751 | 10/1996 |
| WO | WO 2006/122183 | 11/2006 |

* cited by examiner

SOFT TISSUE FILLER

This application claims the priority date of U.S. Provisional Patent Application No. 61/014,282 filed Dec. 17, 2007.

BACKGROUND OF THE INVENTION

The present method refers generally to a soft tissue filler or implant, and more particularly to the injection of a reabsorbable carrier with biocompatible solid particles to correct soft tissue defects and that is applicable for the augmentation of soft tissues. The soft tissue filler is used to even out skin, tissue irregularities, and for the augmentation of human body fat and/or the substitution of human body fat lost due to illness, trauma, aging, or congenital alterations.

In the medical fields of plastic surgery, dermatology and aesthetic medicine, there is currently no injectable long lasting, large volume soft tissue substitute or filler. More particularly, there is currently no injectable large volume soft tissue substitute other than human fat. In that regard, the techniques used to harvest human fat for transfer are generally done with liposuction under a general or local anesthetic, the latter if the amount being harvested is small.

Depending upon the surgeon, the patient and other factors, such as fat harvesting methods and installation techniques, anywhere from 20 to 95 percent of transferred fat is reabsorbed. Therefore, physicians traditionally inject 30% -50% more than is initially needed in order to help make up for what the body will lose. This creates an overfilled look regardless of the site to which the fat is transferred. Because human fat is reabsorbed, an additional supply is generally refrigerated for future use, or, alternatively, the harvesting of fat has to be repeated again.

Additionally, the harvesting of human fat often leaves the harvested area looking slack, uneven and hollowed out, unless of course a major amount of liposuction is conducted for the purpose of local fat reduction. Moreover, human fat harvesting can only work if the patient has sufficient fat to harvest. However, many have none. Also, generally only a small percentage of the installed harvested fat lasts longer than 12 months.

There are several soft tissue augmentation products in the marketplace. However, most such products can only be used in small quantities because they are toxic if used in large quantities. Examples of such augmentation products include "Silskin", "Radiesse" and "Aquamid".

Other soft tissue augmentation products are "Restylane" and "Sculptra". These products are too temporary to be considered for large volume installation. Besides only being applicable for use in small volumes, these products are less than satisfactory due to cost.

Currently, there is only one approved synthetic permanent soft tissue filler in the international market that can be used in large quantities. This soft tissue filler is marketed under the "BioAlcamid" name and is an injectable gel that forms an endoprosthesis. It has, however, a proven history of late adverse reactions such as excessive inflammation and infection as long as five years after implantation. It is also difficult to implant correctly since a defined number of units are necessary in order to create an endoprosthesis that will encapsulate and not be reabsorbed. It cannot be effectively added to at a later time as puncturing the encapsulation will leave the endoprosthesis vulnerable to infection and chronic inflammation.

Further, the encapsulation (endoprosthesis) for carrying the "BioAlcamid" product is approximately 2 mm thick. As a result, the capsule does not allow for blood flow to travel through it, but instead blood travels around it, making it difficult to treat when there is inflammation and or infection. Indeed, the reported late adverse rate for "BioAlcamid" is in excess of 7%. Additionally over time, as skin becomes thinner, with lost elasticity, and as soft tissue diminishes, the outline of the endoprosthesis becomes visually apparent, as does its contents.

Accordingly, it would be desirable to provide a soft tissue filler for augmentation and replacement which overcomes these disadvantages.

SUMMARY OF THE INVENTION

Generally speaking, in accordance with the invention, an improved non-toxic soft tissue filler is provided. The soft non-toxic tissue filler consists of textured surfaced spherically shaped solid particles of a size range of between about 32 and 90 microns (depending on the concentration that is desired) that are suspended evenly in a gel in order to serve as a carrier. The solid particles are preferably a non-ceramic cured polymer such as polymethylmethacrylate (PMMA). The gel is a combination of a cellulose polysaccharide such as carboxymethylcellulose (CMC) and an alcohol such as polyvinyl alcohol (PVA) dissolved in water or some other solvent. The filler is used by injection in order to augment a patient's soft tissue as well as to correct soft tissue defects.

The soft tissue filler of the invention comes in three (3) distinct concentrations of micro-particles suspended in a hydrogel. Other concentrations may be possible in practicing the invention. The soft tissue filler is used to replace and restore tissue lost as a result of congenital or acquired soft tissue deficiencies. Advantageously, implantation of the tissue filler induces the human body to produce a plurality of networks of new organized tissue.

The inventive tissue filler is able to be administered in large quantities in a single and/or multiple applications. This is because PMMA and other similar non-ceramic cured polymer products have been used in medicine for more than 50 years without causing biological degradation, toxicity or cancer.

The inventive tissue filler can be used in a wide spectrum of restorative procedures, ranging from the correction of large deficits such as those found in congenital abnormalities, pectus excavatum, Rombergs syndrome; HIV induced lipoatrophy of the face and body, or those caused by traumas, surgical or accidental. It is also ideally suited for making permanent a wide range of natural looking cosmetic enhancements or corrections so as to minimize the appearance of aging and a non surgical way of correcting anatomical defects that are normally corrected by performing surgical procedures.

Accordingly, it is an object of the invention to provide an improved soft tissue filler.

Another object of the invention is to provide a soft tissue filler that is long lasting.

A further object of the invention is to provide a soft tissue filler which can be used in large quantities.

Yet another object of the invention is to provide a soft tissue filler which produces minimal adverse reactions, both short term and long term.

Still a further object of the invention is to provide a soft tissue filler which produces no allergic reactions and minimizes the risk of infection and inflammation.

Another object of the invention is to provide a soft issue filler product in which particle migration is precluded.

Still other objects and advantages will, in part, be obvious and will, in part, be apparent from the following description.

DETAILED DESCRIPTION OF THE INVENTION

Figure 1:
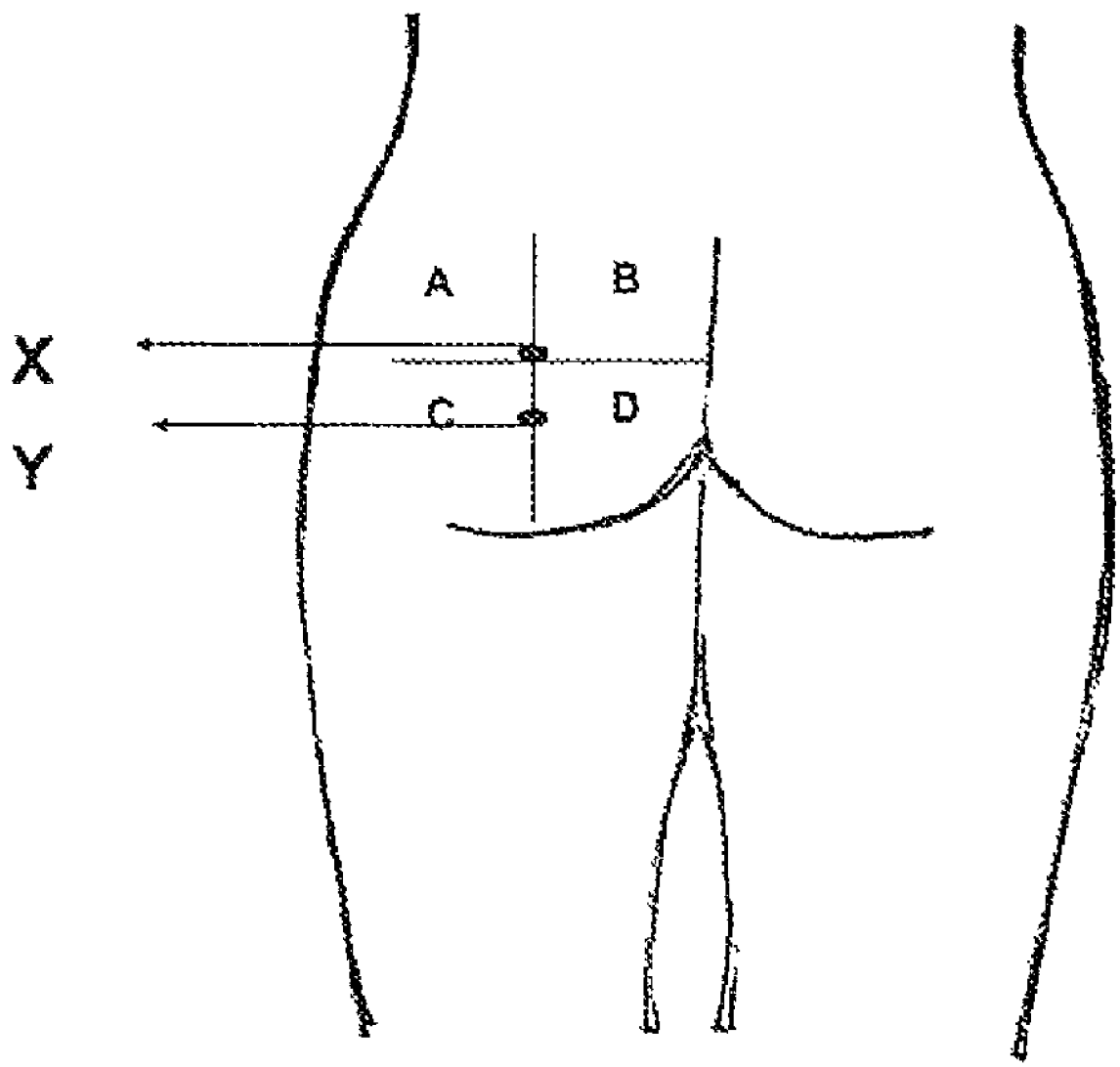
FIG. 1 is a rear view showing a first step in correction of atrophy of the buttocks using the inventive tissue filler.

The inventive soft tissue filler or implant comprises histocompatible solid particles of a non-ceramic cured polymer suspended in a gel/colloid as a carrier. It is designed and developed for exhibiting viscoelastic mechanical properties. The solid particles are suspended evenly in the gel as a result of an agitation process that is performed during addition of the polymer particles to the gel carrier.

The solid particles comprise completely cured and fully polymerized polymers so that no remaining monomers, which may be toxic, are incorporated into the body of the patient being treated. In principle, it is possible to use any histocompatible polymer for producing the polymer particles used in accordance with the invention.

The solid particles are produced with attention to the form, texture, size, diameter and purity of these particles. Test results have shown that all of the solid particles are monomer free (unlike other products), making it a non-toxic product. Test results have also shown that all of the particles have a textured surface with an elliptical or spherical shape. Electron microscopy revealed that the polymer particles have a rough textured surface with small size agglomerate spheres appearing therealong. Because of these characteristics, the particles are long lasting; they are not rejected by the body where implanted, nor are they reabsorbed or washed away through normal lymph or tissue tracts. Also, because of the texture and size of the particles, the body will form smooth soft tissue around them, rather than form harder scar like tissue. Moreover, the chance of capsular contracture is significantly reduced as a result of the textured surface of the particles, thereby creating enhanced soft tissue like volume in the places of implantation.

As stated, the tissue filler or implant of the invention has solid particles of a cured polymer having an elliptical or spherical form. This is because the elliptical or spherical form most closely imitates human cell structure. This is advantageous because tissue growth responds best to what is similar in construction and formation.

The tissue filler or implant of the invention has solid particles of a cured polymer with a size that is sufficiently small so as to be introduced into body tissue without being rejected. Preferably, all of the solid particles have a diameter of between about 32 and 90 microns.

In accordance with the invention, the solid particles are suspended in a physiologically acceptable suspending agent. The suspending agent is a gel or colloid. The gel or colloid predominantly consists of water or some other type of suitable solvent.

The cellulose polysaccharide component of the gel or colloid functions as an emulsifier, thereby promoting even distribution of the gel (which carries the curable polymer micro particles) to the designated physiological site; the cellulose component also reduces the elasticity or rubber like aspects of the alcohol. This is significant since PVA, by itself is very rubbery/elastic and therefore retracts after injection, resulting in constriction and thereby creating a stronger possibility that the growing tissue will harden.

The alcohol facilitates suspension and even distribution of the polymer particles in the gel, thereby creating more uniform tissue production.

In one embodiment, the cured polymer solid particles have a size range in diameter of approximately between about 32 and 52 microns. In a second embodiment, the solid particles have a size range in diameter of approximately between about 53 and 74 microns. In yet a third embodiment, the particles have a size range in diameter of approximately between about 75 and 90 microns.

In accordance with the invention, the tissue filler comprises from between about 10% and 30% (by overall weight) of the cured non-ceramic solid polymer particles. The inventive tissue filler also has a viscosity of between about 6,000 and 20,000 cps.

PMMA and other polymethacrylates are the preferred curable polymers for use in the inventive tissue filler or implant. PMMA is histocompatible and can be incorporated into the human body since it is chemically and physically inert, Other non-ceramic curable polymers may be used instead such as polyethylene, polypropylene, polystyrene, polyacrylamide, polychloroethene, polytetrafluoroethylene, polyacrylonitrile, polyvinylacetate, polycholorprene, polyamides, polyesters, silicones, polyurethanes, polyphosphazenes and biopolymers such as polypeptides.

Manufacture of the inventive tissue filler requires polymerization in order to produce the cured polymer. For PMMA used in the invention, this is achieved by preparing a mixture of polyvinyl alcohol with distilled/sterile water. Separately, the monomer (MMA) is mixed with benzyl peroxide, which will act as initiator of the reaction. In manufacture, both mixtures are kept in agitation on a heated stirring plate for approximately 5 to 8 minutes at 300 to 600 rpm. Once the benzyl peroxide is dissolved, the mixture is added to the water-polyvinyl alcohol mixture in order to create a new mixture. Thereafter, and in order to produce a textured surface on the resulting PMMA particles or powder, sodium lauryl sulfate is added to the new mixture and agitated for 1 to 3 minutes. The stirring speed is then increased to 1000 to 1200 rpm for a duration of 1 to 2 additional minutes in order to achieve polymerization. The mixture is then covered hermetically and is placed in an oven for curing at a temperature of 75 to 80° C. for 6-8 hours.

After curing, the polymerized PMMA is filtered using a standard stainless steel sieve and rinsed with distilled water and alcohol in order to eliminate the monomer remainders and the sodium laurel sulfate. The filtration process is achieved by pouring the polymer into stainless steel electromagnetic sieves of different sizes in order to separate the different size particles that are desired and to be able to discard those sizes that are not suitable. Each of the sieves is shaken mechanically. The result of this procedure is a humid solid powder. Importantly, no mechanical force is applied in order to avoid breaking the spherical form of the filtered polymer (solid) particles resulting in a powder.

After the filtration procedure, the rinsing process begins by placing the solid powder of PMMA particles into a stainless steel container and adding distilled water over a period of between 20 and 40 minutes with vigorous stirring. After 30 minutes of agitation, the powder is left to rest for 10 to 15 minutes so that the polymer precipitates and the water can be decanted. This procedure is repeated several times. The same procedure is repeated several times using alcohol instead of water. Finally, the clean powder is placed into an ultrasonic cleaning machine, and rinsed for 15 to 20 minutes with distilled water. Once rinsed, the powder is placed into a gravity convection oven at a temperature of 60 to 70 degrees C. for a period of 12 to 24 hours to dry.

Thereafter, and before storing, the powder is separated/sieved in an electromagnetic and digital sieving machine of high precision using standard sieves of 90, 75, 53 and 32 microns.

This process ensures that the size of the PMMA particles or powder is the correct size for the production of each of the viscosity specific products. After sieving the solid PMMA particles, they are distributed in three different sizes: 75-90 microns, 53-74 microns and 32-52 microns, and then placed in sterile bottles.

The cellulose component of the gel is biodegradable polysaccharide that will not cause any allergic reaction, can be dissolved in water, has water retention properties, is physiologically inert and is a stabilizing property. The alcohol component of the gel is one that is easily metabolized and eliminated by the body. Both components are compatible when combined and generate a stable gel in which to suspend the solid particles.

In the preferred embodiment, the gel or colloid consists of a mixture of between about 0.5 and 10.0 weight percent of a dissolvable alcohol, 0.5 and 5.0 weight percent of a cellulose polysaccharide, with the balance being water. In its most preferred form, the gel or colloid comprises from between about 2.0 and 2.5 weight percent of cellulose polysaccharide such as CMC and between about 4.0 and 4.5 weight percent of a dissolvable alcohol such as PVA.

In production, the gel ingredients or components are mixed with continuous agitation at a temperature of at least 80° C. in order to obtain a completely homogenous gel or colloid. The mixture is then left to rest for 12 to 24 hours in order to obtain the appropriate gel consistency.

After 12 hours, the gel or colloid goes through a UV disinfection system and is placed in sterile storage units where it is stored at a temperature of approximately 25 to 35° C.

CMC is the preferred cellulose polysaccharide component for the gel or colloid. This is because it is well tolerated by the body and easily disposed of through normal physiological elimination channels. Other suitable cellulose polysaccharides include hydroxypropyl cellulose, methyl cellulose, ethylcellulose and ethylyhydroxy cellulose. Cellulose polysaccarides are particularly advantageous because of their viscoelastic characteristics.

Though less preferred, the cellulose component of the gel may be substituted by some other suitable polysaccharide such as starch, chi-tin, chitosan, an alginate, a carrageen, agar and agarose.

PVA is the preferred dissolvable alcohol component of the gel. This is because it has a long track record of being benign; it is used as an additive in many foods and medicine products.

PVA has the necessary properties for stabilizing the carrier. Specifically, PVA, as a result of its elasticity, increases the viscosity and the "stickiness" of the carrier solution and the particles are therefore maintained in the solution in suspension without dropping to the bottom.

PVA, when dissolved in water, also balances the pH of the gel solution, and therefore there is no need to include additives such as buffers to control the pH.

Other suitable dissolvable alcohols include cetostearyl alcohol and stearyl alcohol.

Water is the solvent of choice for preparing the gel.

Importantly, all materials used in production, including vials, stoppers and caps, are fully sterilized.

The product of the invention is preferably produced in a 100K clean room, using the applicable norms for the manufacture of injectables, and using laminar hood cabinets to assure sterility. Everything that is introduced into the clean room environment is also sterilized.

As previously stated, three different concentrations of the inventive tissue filler product are produced. Each concentration can be used in multiple areas for different types of restoration, augmentation or cosmetic applications.

In accordance with the invention, a 10% concentration has a viscosity of approximately 6500 cps and comprises a mixture of 10% by weight of between about 32 and 52 micron solid particles and 90% gel or colloid. This concentration can be used with a syringe of 1, 3, 5 and 10 ml and with 23 G or 25 G needle. This concentration can be used in the face area or any other areas requiring a small amount of soft tissue filler such as the forehead hollow, temple, brow furrows, eye hollows, other facial hollows, lips lines, crows feet around eyes, marionette line, nasal labial fold and hands.

A 20% concentration has a viscosity of approximately 10,000 cps and comprises a mixture of 20% by weight of between about 53 and 74 micron solid particles and 80% gel or colloid, This concentration can be used with a syringe of 1, 3, 5 and 10 ml and with a 23 G needle or 1.6 cannula, This concentration can be used for the augmentation of the cheek, lip, chin, jaw, chest, hands, calves, ankles, penis (girth only) and filling hollows anywhere on the face or body.

A 30% concentration has a viscosity of approximately 15,000 cps and comprises a mixture of 30% by weight of between about 75 and 90 micron solid particles and 70% gel or colloid. This concentration can be used with 1, 3, 5, and 10 ml syringe and with a 16 G, 18 G or 20 G needle and a 2.4 or 1.6 cannulas. This concentration can be used for augmenting for areas such as the buttocks, male chest and calves or for improving the appearance of damaged muscle or cartilage, or in such cosmetic procedures as lifting the nose tip, giving brows an arch, creating a jaw line of choice, and many other applications.

The inventive soft tissue filler has the following attributes:
pH of 6-7
viscosity which increases proportionally to product concentration
no preservatives nor anesthetic
no components of animal origin
no allergy test required
is easily installed
no hospitalization required
is sterile and without pyrogens
stable at low temperatures (15 to 25 C).
stores at normal room temperatures of approx. 20°-35° C. (68°-95 F.°)
needs no special handling/storing
has long expiration capacity/shelf life The inventive soft tissue filler eliminates the need to harvest fat and serves as a replacement for fat. It does not need to be overfilled because it does not dissipate. This is because there is no break-down, corrosion, or phagocytosis of the micro particles over time.

The inventive soft tissue filler only needs a touch up when the aging process shows or added aesthetics are desired. This is because there is no degradation of the polymer.

The inventive tissue filler has been proven to be non-toxic non-carcinogenic, as the base elements have been used in human bodies in other forms for 50 plus years. The inventive tissue filler has been proven to be long lasting.

In the tissue filler of the invention, particles are suspended evenly in the gel, allowing for even growth of tissue. In accordance with the invention, polymerized particles are used only in specific sizes for specific concentrations as discussed hereinbefore. This is because it has been found that the specific micro particle sizes work best in specific concentrations as there is no macrophage and no large cell development. In this regard, there are three (3) distinct and different viscosities.

The inventive tissue filler eliminates macrophage cells of inflammatory processes and the creation of large cells. This is because the inventive filler is inert. It also produces networks of new organized tissues and prevents the formation of granulomas due to the textured surface of the polymer particles.

Other advantages of the inventive tissue filler include that it can be used anywhere that soft tissue lives or has lived, does not create an outline, can be added to (is accumulative), has no edges or outline, blends with existing tissue, and creates its own vascularity.

Finally, the tissue filler of the invention, when used, creates collagen and elastin in the tissue building process. This is important because this mimics the body's own method of healing and tissue production.

An example of the use of the tissue filler of the invention in the correction of atrophy of the buttocks is as follows:

The patient is placed in anatomical position and the surgical area is marked. As shown in FIG. 1, horizontal and vertical lines are drawn on the buttocks, dividing the area in quadrants with A being the upper external quadrant, B being the upper internal quadrant, C being the lower external quadrant and D being the lower internal quadrant. It is noted that the points of entry will be two, with the first one X including the top quadrants of the upper area and the second one Y including the two lower quadrants of the lower area.

The patient is put on his/her stomach to realize asepsis and antisepsis. Note that sterile gauzes are used with a merthiolate Iodopovidona solution and microcyn (sodium and chlorine) and sterile fields are created.

Figure 2:
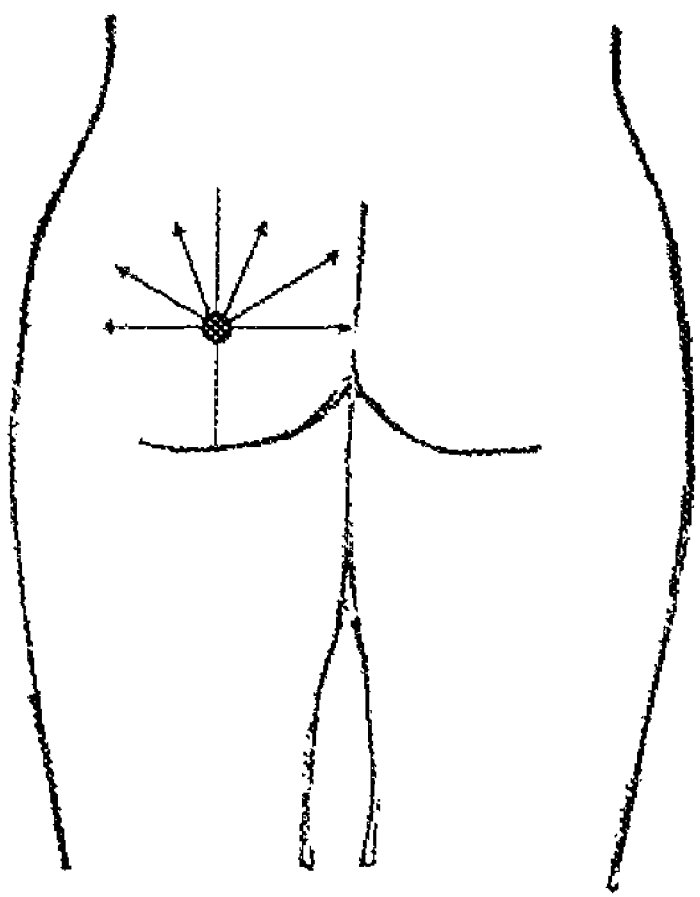
FIG. 2 is a rear view showing progression in correction of atrophy of the buttocks using the inventive tissue filler.
Figure 3:
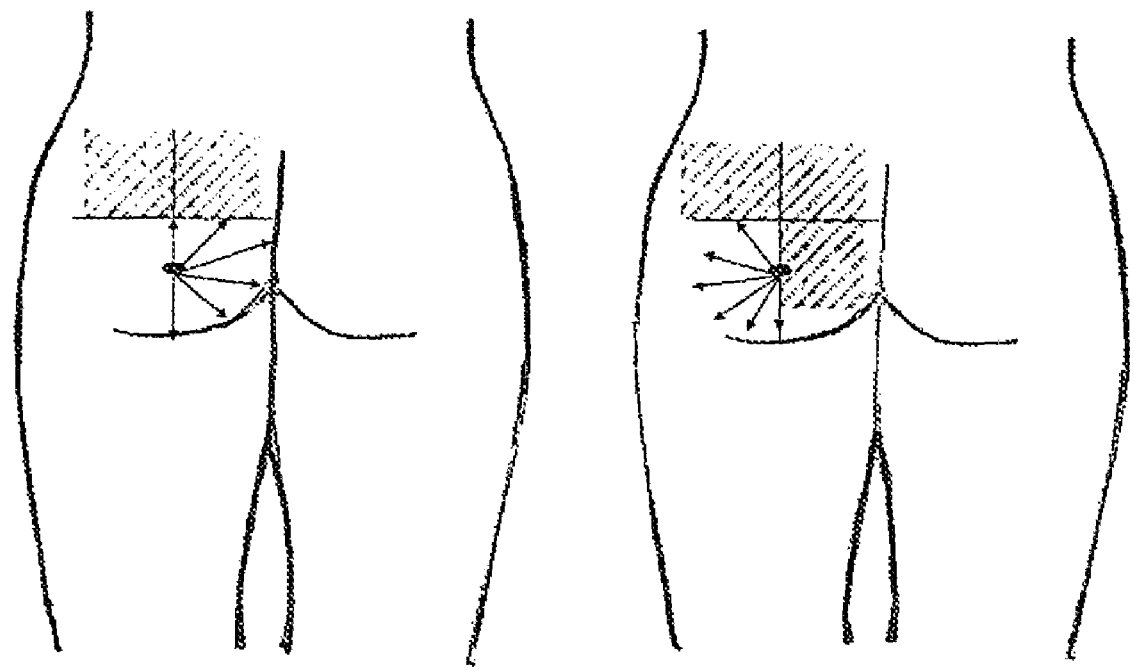
FIG. 3 is a rear view showing a further progression in correction of atrophy of the buttocks using the inventive tissue filler.

After asepsis and antisepsis, anesthesia is applied, in particular lidocaine with epinephrine when applicable, using a syringe at 2 points of entry (see FIG. 1). When the entry points are numb, an orifice with a 16 G needle is made in order to introduce the cannula at the superior entry point. The cannula separates the tissue, preparing it for the installation of the inventive soft tissue filler by injecting the lidocaine while tissue is being separated. The separation of the tissue consists of the introduction of the cannula and moving it, from one side to the other, three or four times in the subcutaneous tissue; the same technique is applied at the inferior entry point. Once the area being treated is fully anesthetized, installation of the inventive soft tissue filler with a cannula attached to a syringe is begun, Syringes are changed while the cannula stays in place. Starting in the top internal quadrant, depositing the filler product from the distal to the proximal part of the entry point is commenced, and continues with the top external quadrant (see FIG. 2) so that the installation follows a uniform evolution. The quantity installed will depend on the degree of lipoatrophy and/or on the volume desired. This technique is repeated for the lower quadrants (see FIG. 3).

Once the procedure is completed, an antibiotic cream is applied with a deep penetrating massage to ensure that the product is distributed uniformly. Thereafter, ultrasound with a medium application head is applied in a circular movement, firstly in the top quadrants and then in the lower ones for a total of 20 minutes per buttock cheek. This is done to smooth the area and to improve the circulation. The mechanism of action of the ultrasound is based on its capacity to transmit energy. This energy causes a thermal effect (anti-inflammatory), as well as an agitating effect, creating analgesia at a low intensity. Bandages are applied on all of the points of entry.

The results of patient evaluation using the preferred inventive tissue filler material (PMMA particles in a gel of CMC and PVA) were extremely positive. 132 patients were evaluated (99 Faces, 18 Buttocks, 4 hands, 1 penis, 1 shoulder, 4 knees, 2 arms, 2 legs, 1 chest). In all cases, there was initial swelling, inflammation and redness at points of entry, occasional bruising and post treatment soreness for about 48 hours. However, there were no infections and no serious adverse reactions.

The scope of the invention will now be found in the following claims.

The invention claimed is:
1. A tissue filler product comprising:
 (a) between about 10 and 30 weight percent of histocompatible solid particles of a non-ceramic curable polymer, the solid particles having a surface that is textured and a diameter of between about 32 and 90 microns; and
 (b) between about 90 and 70 weight percent of degradable gel as a carrier in which said particles are suspended, said gel comprising a polysaccharide as an emulsifier in an amount between about 0.5 and 5.0 weight percent, a dissolvable alcohol in an amount between about 0.5 and 10.0 weight percent, and the balance being water.
2. The product of claim 1, wherein said solid particles have an elliptical or spherical form.
3. The product of claim 1, wherein the solid particles comprise polymethyl methacrylate, the polysaccharide comprises carboxymethyl cellulose, and the alcohol comprises polyvinyl alcohol.
4. The product of claim 1, wherein the curable polymer is selected from the group consisting of polymers of methacrylate.
5. The product of claim 1, wherein the polysaccharide is a cellulose selected from the group consisting of carboxymethyl cellulose, hydroxypropyl cellulose, methyl cellulose and ethylyhydroxy cellulose.
6. The product of claim 1, wherein the polysaccharide is present in an amount between about 2.0 and 2.5 weight percent.
7. The product of claim 1, wherein the alcohol is present in an amount between about 4.0 and 4.5 weight product.
8. The product of claim 1, wherein said solid particles are distributed and suspended substantially evenly in said gel.
9. The product of claim 1, wherein said particles are monomer free.
10. The product of claim 1, wherein the product has a viscosity of between about 6000 and 20,000 cps.
11. The product of claim 1, wherein the alcohol is selected from the group consisting of polyvinyl alcohol, cetostearyl alcohol and stearyl alcohol.
12. A tissue filler product comprising:
 (a) between about 10 and 30 weight percent of polymethyl methacrylate particles having a surface that is textured and having a diameter of between about 32 and 90 microns and
 (b) between about 90 and 70 weight percent of a degradable gel as a carrier in which said particles are suspended, said gel comprising carboxymethyl cellulose as an emulsifier in an amount between about 2.0 and 2.5 weight percent, polyvinyl alcohol in an amount between about 4.0 and 4.5 weight percent, and the balance being water.
13. The product of claim 12, wherein all of said particles have an elliptical or spherical form.

14. A tissue filler system comprising a tissue filler made from histocompatible solid particles of methacrylate polymers suspended in a gel as a carrier and with the solid particles having a surface that is textured; the gel comprising a cellulose polysaccharide as an emulsifier, a dissolvable alcohol, and the balance being water; the tissue filler being in three distinct concentrations with the first concentration comprising said solid particles with a diameter of between about 32 and 52 microns, the second concentration comprising said solid particles with a diameter between about 53 and 74 microns, and the third concentration comprising said solid particles with a diameter of between about 75 and 90 microns.

15. The system of claim 14, wherein said first concentration comprises approximately 10 weight percent of said solid particles and 90 weight percent of said gel, said second concentration comprises 20 weight percent of said solid particles and 80 weight percent of said gel, and said third concentration comprises 30 weight percent of said solid particles and 70 weight percent of said gel.

16. The system of claim 14, wherein the cellulose polysaccharide is present in the gel in an amount between about 0.5 and 5.0 weight percent and the alcohol is present in the gel in an amount between about 0.5 and 10.0 weight percent.

17. The system of claim 14, wherein said solid particles have an elliptical or spherical form.

18. The product of claim 1, wherein the solid particles have an agglomeration of spheres appearing along the surface thereof.

19. The system of claim 14, wherein the solid particles have an agglomeration of spheres appearing along the surface thereof.

20. The product of claim 1, wherein the solid particles are evenly distributed in the gel.

21. The system of claim 14, wherein the solid particles are evenly distributed in the gel.

22. A method for augmenting and/or replacing tissue in a human being, the method comprising:
   (a) suspending histocompatible solid particles of a non-ceramic curable polymer into a degradable gel as a carrier in order to form a tissue filler product, the gel comprising a polysaccharide as an emulsifier in an amount between about 0.5 and 5.0 weight percent, a dissolvable alcohol in an amount between about 0.5 and 10.0 weight percent, and the balance being water; and
   (b) injecting said tissue filler product into a selected tissue location of a human being.

23. The method of claim 20, wherein said tissue filler product comprises between about 10 and 30 weight percent of said solid particles and between about 90 and 70 weight percent of said gel.

* * * * *